United States Patent [19]

Kikkawa

[11] Patent Number: 4,871,355
[45] Date of Patent: Oct. 3, 1989

[54] INJURY RESISTANT NEEDLE AND BLOOD COLLECTION TUBE HOLDER

[76] Inventor: Steven Kikkawa, 15825 Del Prado Dr., Hacienda Heights, Calif. 91745

[21] Appl. No.: 195,072

[22] Filed: May 17, 1988

[51] Int. Cl.4 .............................................. A61M 5/32
[52] U.S. Cl. .................................. 604/198; 604/263; 128/763
[58] Field of Search ............... 604/198, 263, 192, 197, 604/187; 128/763, 764, 765

[56] References Cited

U.S. PATENT DOCUMENTS

| | | | |
|---|---|---|---|
| 2,571,653 | 10/1951 | Bastien | 128/218 |
| 3,304,934 | 2/1967 | Bautista | 128/2 |
| 4,418,703 | 12/1983 | Hoch et al. | 128/766 |
| 4,573,976 | 3/1986 | Sampson et al. | 604/198 |
| 4,731,059 | 3/1988 | Wanderer et al. | 604/192 |
| 4,752,290 | 6/1988 | Schram | 604/198 |
| 4,755,170 | 7/1988 | Golden | 604/52 |
| 4,758,231 | 7/1988 | Haber et al. | 604/198 |

Primary Examiner—John D. Yasko
Attorney, Agent, or Firm—Poms, Smith, Lande & Rose

[57] ABSTRACT

An injury resistant needle and blood collection tube holder which includes an inner tube which telescopes within an outer protective tube. The inner tube is movable between a retracted position wherein the blood collection needle is housed entirely within the outer protective tube and an extended position wherein the needle protrudes for venipuncture. The inner tube is releasably locked in the retracted position to prevent inadvertent disengagement of the protective outer tube. The annular ridges are provided on the tubes to facilitate single-handed operation of the device.

12 Claims, 2 Drawing Sheets

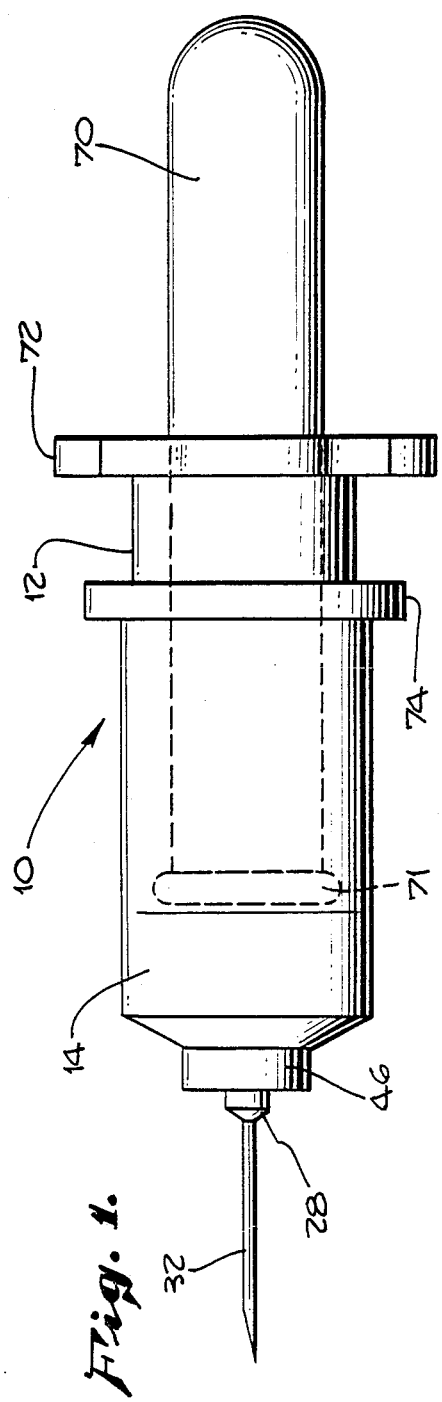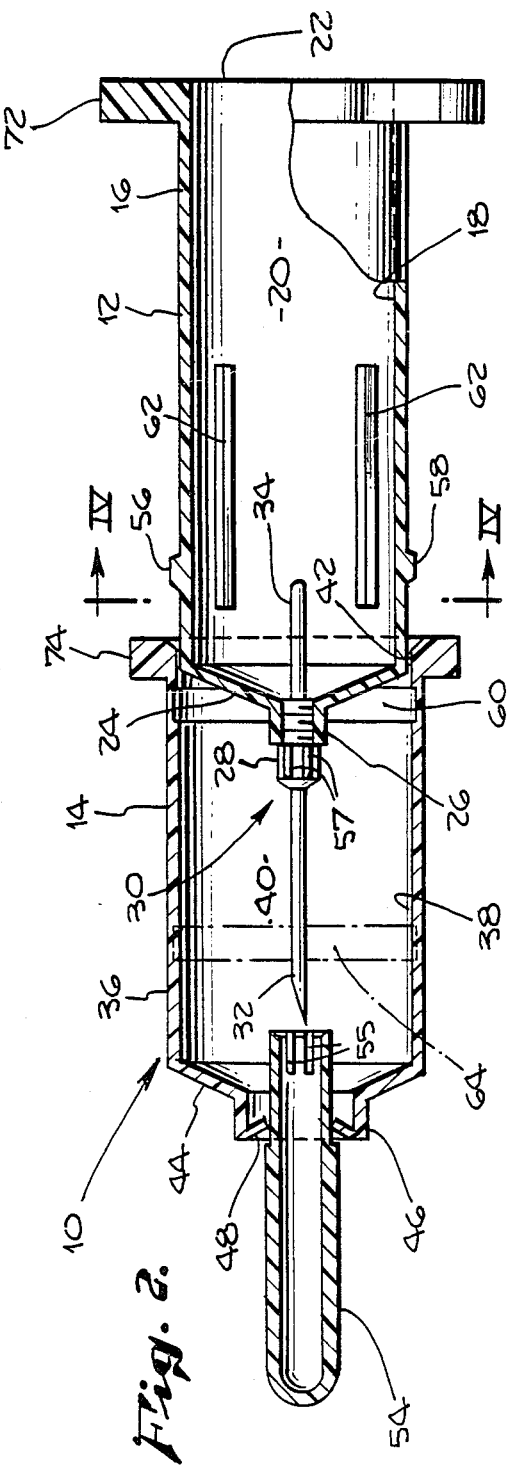

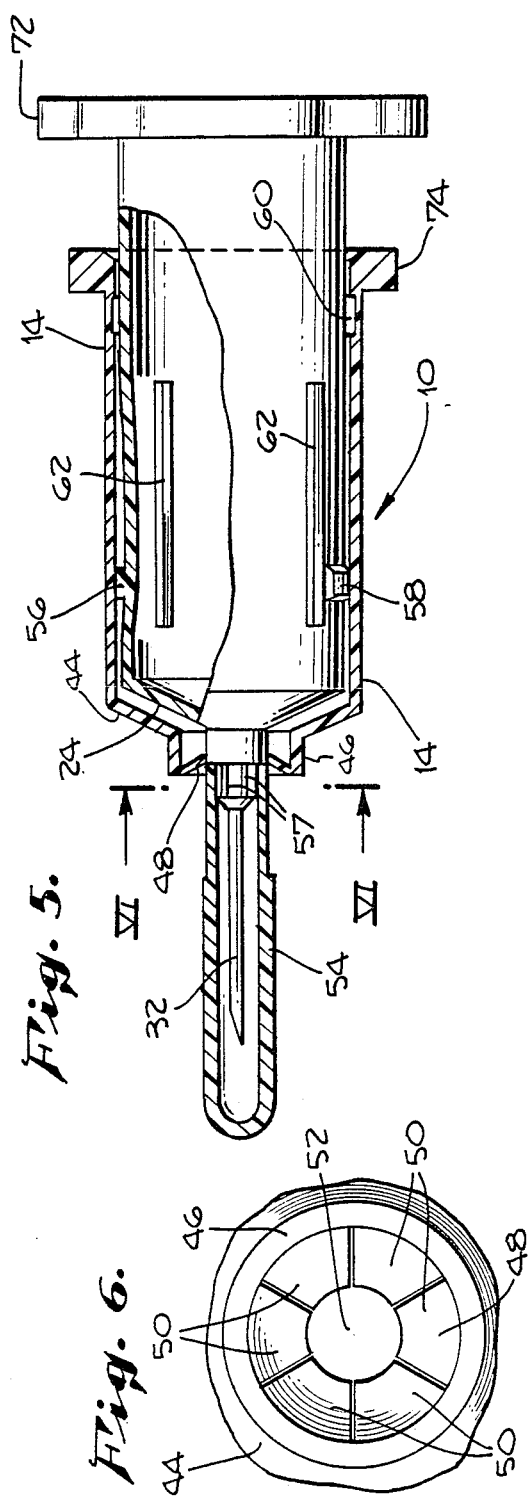

INJURY RESISTANT NEEDLE AND BLOOD COLLECTION TUBE HOLDER

BACKGROUND OF THE INVENTION

1. Field of the Invention

The present invention relates to needle and blood collection tube holders which are used in collecting multiple samples of blood. More particularly, the invention relates to an improved needle and blood collection tube holder which is designed to provide a protective covering over contaminated needles to reduce the possibility of accidental piercing of a health worker's skin by the contaminated needle.

2. Description of Related Art

Standard clinical laboratory and hospital procedures include a practice of collecting multiple samples of blood from a patient in a single medical procedure. This multiple sample collection procedure generally involves the use of a blood collection needle, one or more blood collection tubes, and a holder for holding the needle and blood collection tubes during the blood collection process.

The blood collection tubes are typically glass or plastic tubes of varying sizes which have a rubber stopper or septum. The blood collection tubes are evacuated so that a vacuum exists within the tube. The blood collection needles have a centrally located collar which is adapted to be screwed or otherwise releasably attached to the blood collection tube holder. This centrally located collar divides the blood collection needle into two portions: a forward end which is adapted to be inserted into the patient and a rear end which is adapted to puncture the septum of the blood collection tube.

The holder for the blood collection tubes and needle is generally a plastic tube which is similar to a syringe in shape. During collection of blood, the blood collection needle is attached to the front end of the holder and a blood collection tube is inserted into the holder so that the septum of the blood collection tube is located next to the rear end of the blood collection needle. The forward end of the blood collection needle is inserted into the patient's vein and at the same time the blood collection tube is forced against the rear end of the blood collection needle so as to insert the needle through the blood collection tube septum. The vacuum within the blood collection tube provides sufficient suction to withdraw blood from the pierced vein. The blood collection tube is removed and any number of additional tubes may be inserted into the holder, pierced by the needle, and filled with blood.

After completion of blood collection, the needle is removed from the patient's vein and covered with a protective sheath. Prior to covering with the protective sheath, the exposed contaminated needle presents a health threat to the laboratory technologist or technician because of possible inadvertent puncture or contact. The possible threat of inadvertent needle puncture or other contact becomes especially important in view of modern day blood-transmitted diseases, such as hepatitis or AIDS.

The problem presented by a contaminated needle has been recognized and addressed in U.S. Pat. No. 4,573,976. This patent, however, is directed to a disposable hypodermic syringe used for the injection of various substances into humans and animals. Hypodermic syringes are generally designed for single use applications and are fully disposable. This is to be contrasted with needle and blood collection tube holders which are designed to receive multiple tubes for collecting multiple samples of blood.

There presently is a need to provide a needle and blood collection tube holder which provides protection against inadvertent puncture or contamination of the health worker prior to, during, and after collection of blood samples.

SUMMARY OF THE INVENTION

In accordance with the present invention, an injury resistant needle and blood collection tube holder is disclosed which provides a way for the health worker to substantially reduce the chance of accidental contact with the blood collection needle after the needle is removed from the patient's arm.

The present invention is based on a needle and blood collection tube holder which includes an inner tube having a cylindrical exterior surface and an interior cylindrical surface defining a blood collection tube receptacle chamber having a longitudinal axis. The inner tube has an open rear end through which the blood collection tubes are introduced into the receptacle chamber and a restricted forward end to which the collection needle is mounted.

As a feature of Applicant's invention, an outer tube having a cylindrical exterior surface and an interior cylindrical surface defining a needle protection chamber is provided. The outer tube has a diameter of sufficient size to matingly receive the inner tube therein. The outer tube includes an open rear end through which the inner tube is introduced into the needle protection chamber and a restrictive forward end which is capable of receiving and holding a protective needle sheath. The outer tube is of sufficient longitudinal length so that the needle is housed completely within the outer tube's needle protection chamber when the inner tube is moved to a retracted position in which the forward end of the inner tube is located at or near the rear end of the outer tube.

In accordance with the present invention, the inner tube is moved to an extended position wherein the forward end of the inner tube is located at or near the forward end of the outer tube. In this extended position, the blood collection needle protrudes from both the inner and outer tubes to allow insertion of the needle for blood collection. After blood collection has been completed, the inner tube is withdrawn to the above-mentioned retracted position wherein the blood collection needle is housed completely within the outer tube needle protection chamber. The telescoping extension and retraction of the inner tube within the outer tube provides a simple, convenient, and reliable means for protecting the health worker from accidental injury or exposure to disease due to inadvertent contact with the contaminated needle.

As a feature of the present invention, the inner tube and outer tube have structures on their respective exterior and interior surfaces which provide for releasable locking of the inner tube in the extended and retracted positions. A further feature involves providing annular ridges extending radially outward from the rear ends of the inner and outer tubes. These annular ridges facilitate manual grasping of the inner and outer tubes so that single-handed operation of the device between extended and retracted positions is possible. The single-handed operation of the holder is an important advantage in collecting blood samples since it is desirable to have one hand free for applying and removing tourniquets, cleaning the needle puncture site and applying antiseptics and/or bandages to the puncture wound.

As another feature of the present invention, the forward end of the outer tube includes a flexible diaphragm which is capable of holding protective sheaths of different diameters. The diaphragm is constructed to not only hold the protective sheath, but to allow insertion of the sheath into the needle protection chamber. This allows the health worker to insert the sheath over the blood collection needle while the needle is in the needle protection chamber. This procedure allows the health worker to cover the needle without the risk of inadvertent puncture. The inner tube can then be moved to the extended position wherein the needle covered with the needle sheath can be disengaged from the inner tube and discarded.

The above discussed and many other features and attendant advantages of the present invention will become apparent as the invention becomes better understood by reference to the following detailed description when considered in conjunction with the accompanying drawings.

BRIEF DESCRIPTION OF THE DRAWINGS

FIG. 1 is a side elevational view of a preferred exemplary needle and blood collection tube holder in accordance with the present invention. The holder is shown during the blood collection procedure wherein the blood collection tube is inserted within the holder.

FIG. 2 is a side sectional view of the preferred exemplary holder showing the inner tube being inserted into the outer tube.

FIG. 3 is a side elevational view of the inner tube with the needle and sheath in place. This view demonstrates manual compression of the tabs on the inner tube prior to insertion of the inner tube into the outer tube.

FIG. 4 is a sectional view of FIG. 2 taken in the IV—IV plane.

FIG. 5 is a side sectional view showing the inner tube at the extended position relative to such outer tube.

FIG. 6 is a view of FIG. 5 taken in the VI—VI plane showing a preferred exemplary diaphragm configuration.

DESCRIPTION OF THE PREFERRED EMBODIMENTS

A preferred exemplary needle and blood collection tube holder in accordance with the present invention is shown generally at 10 n FIGS. 1, 2, and 5. As best shown in FIG. 2, the holder 10 includes an inner tube 12 and an outer tube 14. The tubes can be made from any of the conventional materials utilized for making needle and blood collection tube holders. Typically, these materials are plastics, which are strong, lightweight and inert with respect to blood and other liquids. The preferred plastic materials are polypropylene and similar plastics which are conventionally known and used in the art.

The inner tube 12 includes a cylindrical exterior surface 16 and an interior cylindrical surface 18. The interior cylindrical surface 18 defines a blood collection tube receptacle chamber 20. The inner tube 12 has an open rear end 22 and a restricted forward end 24. The forward end includes an annulus 26 which is threaded on its interior surface for receiving the threaded collar 28 of the blood collection needle 30.

The blood collection needle 30 includes a forward end 32 which extends outwardly along the longitudinal axis of the inner tube 12 and a rearward end 34. The blood collection needle is of conventional design with the forward end 32 designed for piercing the patient's vein and the rearward end 34 being designed for piercing the rubber septum of a standard blood collection vial or tube.

The inner tube 12 is designed to be inserted into the outer tube 14. The outer tube 14 includes an exterior surface 36 and an interior cylindrical surface 38. The interior cylindrical surface 38 defines a needle protection chamber 40. The outer tube 14 also includes an open rear end 42 and a restricted forward end 44. The restricted forward end 44 includes an annulus 46 which has a diaphragm 48 mounted thereto.

The diaphragm 48 is best shown in FIG. 6. The diaphragm 48 is preferably made from a resilient material such as resilient plastic or rubber. The diaphragm 48 includes individual sections or leafs 50 which are sufficiently flexible so that the central orifice 52 can be expanded to receive protective sheaths of different sizes. Referring to FIG. 2, a protective sheath 54 is shown inserted within the orifice 52. The diaphragm leafs 50 provide a means for centering and holding the protective sheath 50 within the annulus 46. As is conventional, the protective sheath 54 is provided with ridges 55 that are designed to engage mating locations between ridges 57 on needle collar 28. This engagement allows the blood collection needle to be conveniently screwed into the inner tube annulus 26 prior to blood collection and unscrewed from the annulus after completion of the blood collection procedure.

Retracted position locking means are included to provide releasable locking of the inner tube 12 to the outer tube 14 when the inner tube is in a retracted position. This locking means includes tabs 56 and 58 and which are located on the exterior surface 16 of the inner tube. The inner tube is provided with adequate resiliency so that tabs 56 and 58 may be compressed sufficiently to allow the inner tube 12 to be inserted into the needle protection chamber.

The tabs 56 and 58 are designed to releasably interlock with groove 60 in the outer tube 14. The expansion of tabs 56 and 58 into groove 60 provides releasable locking of the inner tube 12 at a retracted position wherein needle 32 is completely housed within the needle protection chamber 40. Locking of tabs 56 and 58 within groove 60 can be overcome by pushing or pulling the inner tube 12 with an additional amount of force sufficient to overcome the locking engagement. Alternatively, the inner tube 12 can be compressed to remove the tabs 56 and 58 from groove 60.

Longitudinal slits 62 are provided at both ends of tabs 56 and 58 to provide easier compression of the tabs for release from groove 60. The tab and slit arrangement and the method by which tabs are compressed for insertion into the outer tube is best shown in FIGS. 3 and 4.

When the inner tube 12 is pushed forward to the extended position as shown in FIG. 5, the compression of tabs 56 and 58 against the interior wall 38 of the outer tube 14 provides sufficient resistance to give a certain amount of releasable locking of tube 12 in the extended position. Alternatively, a groove 64 (shown in phantom in FIG. 2) can be provided to increase the amount of force necessary to unlock the inner tube from the extended position as shown in FIG. 5.

Operation of the exemplary needle and blood collection tube holder is as follows: the tabs 56 and 58 on inner tube 12 are compressed as shown in FIG. 3 and the inner tube is inserted into the outer tube 14 to the extended position as shown in FIG. 5. The inner and outer tubes may be stored separately or the entire assembly as shown in FIG. 5 may be stored and/or sold as a single unit.

In order to obtain a blood sample, a standard blood collection tube or vial 70 is inserted into the inner tube as shown in FIG. 1 Just prior to venipuncture, the needle sheath 54 is removed and venipuncture accomplished. Upon venipuncture, the blood collection tube 70 is moved forward so that needle portion 34 punctures the rubber septum 71 to allow transfer of blood into the evacuated blood collection tube. The diameter of the holder can be any size necessary to receive the usual sized blood vacuum containers or collection tubes conventionally used.

After one or more samples have been collected, the needle 32 is removed from the vein and simultaneously the inner tube 12 is moved to the retracted position wherein tabs 56 and 58 are seated within groove 60. At this point, needle 32 is completely housed within needle protection chamber 40. The needle 32 is then resheathed by inserting the sheath 54 through orifice 52 in the diaphragm 48. The sheath 54 can be inserted completely through orifice 52 onto the needle 32. However, it is preferred to only partially insert the sheath 54 and then move the inner tube to the extended position to complete sheathing of needle 32. At this point, the needle may be removed from the holder and discarded. The holder is then ready to receive the next uncontaminated needle for use in drawing a subsequent blood sample.

In carrying out the blood drawing operation, it is desirable that operation of the needle and blood collection tube holder be conducted with one hand. Accordingly, the inner tube 12 is provided with an annular ridge 72 and outer tube 14 is provided with an annular ridge 74. These annular ridges facilitate manual grasping of the tubes during one-hand operation to provide easy manipulation of the inner tube between the extended and retracted positions previously described.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiment as illustrated herein but is only limited by the following claims.

What is claimed is:

1. An injury resistant needle and blood collection tube holder adapted for use in collecting multiple blood samples comprising:

an inner tube having a cylindrical exterior surface and an interior cylindrical surface defining a blood collection tube receptacle chamber having a longitudinal axis, said inner tube having an open rear end through which the blood collection tubes are introduced into said receptacle chamber and a restricted forward end including means for mounting a needle to said forward end, said needle having a forward end extending outwardly along said chamber longitudinal axis and a rearward end extending into said chamber along said longitudinal axis when said needle is mounted to said inner tube forward end;

an outer tube having a cylindrical exterior surface and an interior cylindrical surface defining a needle protection chamber having a longitudinal axis and a diameter of sufficient size to receive said inner tube therein, said outer tube having an open rear end through which said inner tube is introduced into said needle protection chamber and a restricted forward end including a resilient diaphragm having a central opening and radially extending slits whereby needle sheaths of varying diameters may be inserted into said central opening, said diaphragm being sufficiently resilient to provide holding of said sheaths within said central opening, said outer tube being of sufficient longitudinal length so that said needle forward end is housed completely within said needle protection chamber when said inner tube forward end is located in a retracted position towards said outer tube rear end, said inner tube being movable within said outer tube between said retracted position where said needle forward end is housed within said needle protection chamber to prevent accidental injury by said needle and an extended position wherein said inner tube forward end is extended into said outer tube and located toward said outer tube forward end to expose said needle for use in collecting blood; and retracted position locking means for releasably engaging said inner tube to said outer tube when said inner tube is located in said retracted position to prevent said inner tube from being completely removed from said outer tube.

2. An injury resistant needle and blood collection tube holder according to claim 1 wherein said retracted position locking means comprises:

as surface defining an annular groove in the interior cylindrical surface of said outer tube located at the outer tube rear end;

detent means located on the exterior surface of said inner tube at said forward end for engaging said annular groove to provide locking of said inner tube within said outer tube when said inner tube is in said retracted position; and release means for engaging and disengaging said detent means from said annular groove whereby said detent means is disengaged from said annular groove when said inner tube is moved to said extended position.

3. An injury resistant needle and blood collection tube holder according to claim 2 wherein said detent means comprises a detent tab extending radially outward from the forward end of said inner tube exterior surface.

4. An injury resistant needle and blood collection tube holder according to claim 2 wherein aid detent means comprises two detent tabs extending radially outward from opposite sides of the forward end of said inner tube exterior surface.

5. An injury resistant needle and blood collection tube holder according to claim 3 wherein said release means comprises two longitudinal slits in said inner tube wherein one slit extends on one side of said detent tab and the other slit extends on the opposite side of said detent tab to provide sufficient inward resilient compressibility of said detent tab to disengage said detent tab from said annular groove.

6. An injury resistant needle and blood collection tube holder according to claim 4 wherein said release means comprises four longitudinal slits in said inner tube wherein one slit extends on either side of each of said detent tabs to provide sufficient inward resilient compressibility of said detent tabs to disengage said detent tabs from said annular groove.

7. An injury resistant needle and blood collection tube holder according to claim 1 further including extended position locking means for releasably engaging said inner tube to said outer tube when said inner tube is located in said extended position.

8. An injury resistant needle and blood collection tube holder according to claim 7 wherein said extended position locking means comprises:
   a surface defining an annular groove in the interior cylindrical surface of said outer tube located at the outer tube forward end;
   detent means located on the exterior surface of said inner tube at said forward end for releasably engaging said annular groove to provide releasably locking of said inner tube to said outer tube when said inner tube is in said extended position.

9. An injury resistant needle and blood collection tube holder according to claim 8 wherein the detent means for engaging the annular groove at said outer tube forward end comprises a detent tab extending radially outward from the forward end of said inner tube exterior surface, said detent being sufficiently compressible inwardly to provide releasable snap fitting of said detent tab within said outer tube forward end annular groove.

10. An injury resistant needle and blood collection tube holder according to claim 1 wherein said inner tube includes an annular ridge extending radially outward from the rear end of said inner tube to facilitate manual grasping of said inner tube when moving said inner tube between said retracted and extended positions.

11. An injury resistant needle and blood collection tube holder according to claim 1 wherein said outer tube includes an annular ridge extending radially outward from the rear end of said outer tube to facilitate manual grasping of said outer tube when moving said inner tube between said retracted and extended positions.

12. An injury resistant needle and blood collection tube holder according to claim 1 wherein said inner and outer tubes are made from polypropylene.

* * * * *